(12) United States Patent
Ruehling et al.

(10) Patent No.: US 10,772,954 B2
(45) Date of Patent: Sep. 15, 2020

(54) DUAL ADJUVANT VACCINE COMPOSITIONS, PREPARATION AND USES

(71) Applicant: Biomune Company, Lenexa, KS (US)

(72) Inventors: Roger H. Ruehling, Overland Park, KS (US); Brianna Ford, Lenexa, KS (US)

(73) Assignee: Biomune Company, Lenexa, TX (US)

( * ) Notice: Subject to any disclaimer, the term of this patent is extended or adjusted under 35 U.S.C. 154(b) by 0 days.

(21) Appl. No.: 15/316,673

(22) PCT Filed: Jun. 15, 2015

(86) PCT No.: PCT/US2015/035742
§ 371 (c)(1),
(2) Date: Dec. 6, 2016

(87) PCT Pub. No.: WO2015/195504
PCT Pub. Date: Dec. 23, 2015

(65) Prior Publication Data
US 2017/0196972 A1    Jul. 13, 2017

Related U.S. Application Data (63) Continuation of application No. 14/305,329, filed on Jun. 16, 2014, now abandoned.

(51) Int. Cl.
| | |
|---|---|
| *A61K 39/112* | (2006.01) |
| *A61K 45/00* | (2006.01) |
| *A61K 47/00* | (2006.01) |
| *A61K 39/00* | (2006.01) |
| *A61K 39/38* | (2006.01) |
| *A61K 39/39* | (2006.01) |
| *A61K 9/107* | (2006.01) |

(52) U.S. Cl.
CPC .............. *A61K 39/39* (2013.01); *A61K 9/107* (2013.01); *A61K 39/0275* (2013.01); *A61K 2039/521* (2013.01); *A61K 2039/522* (2013.01); *A61K 2039/552* (2013.01); *A61K 2039/55505* (2013.01); *A61K 2039/55566* (2013.01); *Y02A 50/482* (2018.01)

(58) Field of Classification Search
CPC .............. A61K 39/39; A61K 2039/522; A61K 39/0275
See application file for complete search history.

(56) References Cited

U.S. PATENT DOCUMENTS

| | | | | |
|---|---|---|---|---|
| 4,069,313 A | * | 1/1978 | Woodhour | A61K 9/0019 424/209.1 |
| 5,424,067 A | * | 6/1995 | Brancq | A61K 9/113 424/184.1 |
| 5,622,649 A | | 4/1997 | Hunter et al. | |
| 5,817,320 A | | 10/1998 | Stone | |
| 8,444,993 B2 | | 5/2013 | Huang et al. | |
| 9,107,831 B2 | * | 8/2015 | O'Hagan | A61K 9/1641 |
| 2002/0051748 A1 | | 5/2002 | Snow et al. | |
| 2005/0158330 A1 | * | 7/2005 | Saito | A61K 9/113 424/184.1 |
| 2006/0233831 A1 | * | 10/2006 | Parisot | A61K 39/39 424/204.1 |
| 2008/0220022 A1 | * | 9/2008 | Le Gros | A61K 39/0275 424/258.1 |
| 2011/0280949 A1 | * | 11/2011 | Malyala | A61K 9/19 424/501 |
| 2014/0099358 A1 | | 4/2014 | Brown et al. | |

FOREIGN PATENT DOCUMENTS

| | | |
|---|---|---|
| EP | 640348 A1 | 3/1995 |
| EP | 1097721 A2 * | 9/2001 |
| JP | 2002080396 * | 3/2002 |

OTHER PUBLICATIONS

Pandit et al., Journal of Microencapsulation, 2007; 24(6): 539-552.*
Freund et al "Sensitization to Horse Serum by Means of Adjuvants" Proceedings of the Society for Experimental Biology and Medicine vol. 49, pp. 548-553. 1942.
Matsumoto et al "A Broth Bacterin Against Infectious Coryza: Immunogenicity of Various Preparations" Avian Diseases vol. 15, pp. 109-117. 1971.
Reid et al "Comparison of Adjuvants for an Inactivated Infectious Coryza Vaccine" Avian Diseases vol. 31, pp. 59-63. 1987.
Blackall et al "An Evaluation of Inactivated Infectious Coryza Vaccines Containing a Double-Emulsion Adjuvant System" Avian Diseases vol. 36, pp. 632-636. 1992.
Blackall "Vaccines Against Infectious Coryza" World's Poultry Science Journal vol. 51, pp. 17-26. 1995.
Bidin et al "Protection of Broiler Breeders by an Inactivated Combined Water-in-Oil-in-Water Viral Vaccine" Acta Veterinaria Hungarica vol. 46, pp. 25-34. 1998.
Jiao et al "Rheology and Stability of Water-in-Oil-in-Water Multiple Emulsions Containing Span 83 and Tween 80" AAPS PharmSci vol. 5, pp. 62-73. 2003.
Pandit et al "Enhancement of Immune Response of HBsAg Loaded Poly(L-lactic Acid) Microspheres Against Hepatitis B Through Incorporation of Alum and Chitosan" Journal of Microencapsulations vol. 24, pp. 539-552. 2007.
Ye et al "Issues in Long-Term Protein Delivery Using Biodegradable Microparticles" Journal of Controlled Release vol. 146, pp. 241-260. 2010.

* cited by examiner

*Primary Examiner* — Gary B Nickol
*Assistant Examiner* — Lakia J Jackson-Tongue
(74) *Attorney, Agent, or Firm* — Cesari & McKenna, LLP (57) ABSTRACT

The present invention relates to vaccines comprising an effective amount of at least one antigen in a water-in-oil-in-water (WOW) emulsion and an additional adjuvant, and to the methods of preparation and uses thereof.

13 Claims, 6 Drawing Sheets

DUAL ADJUVANT VACCINE COMPOSITIONS, PREPARATION AND USES

CROSS REFERENCE TO RELATED APPLICATIONS

This application is the National Stage of International Application No. PCT/US2015/035742, filed on Jun. 15, 2015, which claims the benefit of U.S. application Ser. No. 14/305,329, filed on Jun. 16, 2014. The contents of both applications are hereby incorporated by reference in their entirety.

The present invention relates to vaccines, their preparation and uses. The invention more specifically relates to dual adjuvant vaccines comprising at least one antigen in a water-in-oil-in-water (WOW) emulsion and an additional adjuvant. The vaccines of the invention may comprise any type of antigen, preferably bacterial antigens, and are particularly adapted for veterinary use, such as for vaccinating chickens.

BACKGROUND OF THE INVENTION

Vaccines are usually formulated with an adjuvant to enhance and improve the immune response, notably to prolong antibody response. For instance, Freund's adjuvant (Proceedings of The Society for Experimental Biology and Medicine, 1942, 49, 548-553), which corresponds to a solution of antigen emulsified in mineral oil, has first been used as an immunopotentiator or as an immunobooster. Freund's adjuvant forms a water-in-oil (WO) emulsion and exhibits an adjuvant effect essentially through a sustained release of the antigen.

Various other adjuvant systems have been evaluated in order to provide effective vaccines. These include, for instance, chitosan, cytokines, oligonucleotides, lipids, toxins, hapten carriers or aluminum hydroxide. In this regard, Matsumoto et al. (Avian diseases, 1971, 15, 109-117) has tested the efficacy of aluminum derivate such as aluminum hydroxide gel and chrome aluminum in vaccines. Blackall et al. (Avian Diseases, 1992, 36, 632-636) have compared aluminum-hydroxide adjuvant and WO emulsions. Squalene, saponin, Quil A, lipoidal amine, glycan or avridine have also been added as adjuvants to vaccines to improve their efficacy.

EP 0 640 348 relates to a vaccine comprising a WO emulsion and an immunostimulatory glycan. US 2014/0099358 proposes a vaccine comprising a water-in-oil emulsion and aluminum or a compound of aluminum or TiterMax (squalene). However, the design of combined emulsion-adjuvant systems generates safety issues because of possible side effects (Reid and Blackall, Avian Diseases, 1987, 31, 59-63). Furthermore, traditional WO emulsions often have a high viscosity and are difficult to formulate or inject.

Vaccines based on WOW emulsions have been tested in in ovo immunization of avian embryos (U.S. Pat. No. 5,817,320) and against specific viruses such as Newcastle disease virus, infectious bronchitis virus (Cajavec et al., Acta Veterinaria Hungarica, 1998, 46, 25-34), and infectious Coryza (Blackall, World's Poultry Science Journal, 1995, 51, 17-26).

Such vaccines in a WOW emulsion have also been improved in term of stability according to the nature and the proportions of the surfactants used to produce the WOW emulsion. In this context, Hunter and Bennet have studied the polyoxyethylene polyoxypropylene block copolymer of formula $HO(C_2H_4O)_b(C_3H_6O)a(C_2H_4O)_b$ at Hydrophilic-Lipophilic Balance (HLB) below 2 (U.S. Pat. No. 5,622, 649). They have also tested such WOW emulsions in vaccination methods for Hepatitis B infection and have mentioned their effectiveness against tetanus, malaria, AIDS, influenza and pneumococcal pneumonia.

Jiao and Burgess (AAPS Pharm. Sci., 2003, 5, 1-12) have evaluated the long-term stability of WOW multiple emulsions with respect to the concentrations of two specific surfactants, Span 83 and Tween 80, and have determined that a concentration ratio of 20% Span 83 and 0.1% Tween 80 provided the best long-term stability of WOW emulsions. WOW emulsions, however, do not always generate satisfactory immune response. In addition, WOW may be associated to a number of potential disadvantages including their lack of homogeneity, for instance in the size distribution profile of particles, and the possible viscosity of heterogeneous formulations. Furthermore, there is no established suitability of such systems for formulating large objects such as cells.

Accordingly, there is a need in the art for alternative, safe and improved vaccines, notably for use in animals.

SUMMARY OF THE INVENTION

The invention provides novel vaccines having improved efficacy. The invention particularly discloses a dual adjuvant system vaccine which combines a WOW emulsion and an adjuvant compound. The invention stems from the unexpected finding by the inventors that such dual-adjuvant systems are safe and generate improved immune response in vivo. In particular, the invention shows that such vaccines induce potent protective immune responses in non-human animals and are particularly suited for bacterial antigens, preferably including whole cell bacteria.

An object of the invention therefore relates to a vaccine comprising an effective amount of at least one antigen in a water-in-oil-in-water (WOW) emulsion and an additional adjuvant.

Another object of the invention relates to a vaccine comprising an effective amount of at least one antigen and an adjuvant compound in a water-in-oil-in-water (WOW) emulsion.

Another object of the invention is a vaccine as defined above for use to induce an immune response against said antigen in a non-human animal.

A further object of the invention relates to a method for inducing an immune response against an antigen in a non-human animal, comprising administering to said animal a composition comprising an effective amount of said at least one antigen in a WOW emulsion and an additional adjuvant.

Another object of the invention is a process for the preparation of a vaccine comprising:

a) emulsifying a solution of at least one antigen in an oil base, thereby forming a WO emulsion, b) adding said WO emulsion to a dispersal phase, thereby forming a WOW emulsion and, optionally, further emulsifying said WOW emulsion, and c) mixing said WOW emulsion with an additional adjuvant, preferably in combination with a further amount of said at least one antigen.

In a particular embodiment, the additional adjuvant is aluminum hydroxide.

In another particular embodiment, the at least one antigen is a bacterial antigen, preferably a live, attenuated, or inactivated bacterium.

In a particular aspect of the invention, the vaccine as defined above comprises said antigen embedded in oily particles, preferably having a size between 1 and 40 μm.

As will be disclosed further, the compositions of the invention are particularly suited to vaccinate non-human animals, particularly poultry (e.g., chickens, waterfowl) or birds.

DETAILED DESCRIPTION OF THE INVENTION

The invention provides novel and improved vaccine compositions, methods of preparation thereof and their uses. The invention particularly discloses novel vaccines comprising an effective amount of at least one antigen in a WOW emulsion and further comprising an adjuvant. The invention stems from the unexpected finding, by the inventors, that such a dual-adjuvant system is easily syringable, safe, and provides greater efficacy (protective immunity) than prior art vaccines using other adjuvant systems. Particularly, the inventors have demonstrated a synergistic effect for the vaccines of the invention comprising at least one antigen and a dual-adjuvant system. The inventors have also demonstrated an improved protection efficacy against *salmonella* infection in vivo of such vaccines, as well as their safety.

An object of the invention therefore relates to a vaccine or composition comprising an effective amount of at least one antigen in a WOW emulsion and an additional adjuvant.

Another object of the invention is a vaccine or immunogenic composition comprising an antigen and an additional adjuvant in a WOW emulsion, wherein the antigen is included in oily particles comprising an inner aqueous phase and an oily phase, and wherein the additional adjuvant is included in an outer aqueous phase, preferably complexed with the antigen.

Another object of the invention is a vaccine or immunogenic composition comprising whole cells in a WOW emulsion, wherein at least 90% of the oily particles in the WOW emulsion have a size below 20 μm, the composition has an OD600/ml superior to 4, and at least 60% of the cells in the composition are contained in said oily particles.

A further object of the invention is a method for inducing an immune response against at least one antigen in a non-human animal, comprising administering to the animal a vaccine or composition comprising an effective amount of said at least one antigen and an adjuvant compound in a WOW emulsion.

A further object of the invention is a method for vaccinating a non-human animal against a pathogen, comprising administering to the animal a vaccine or composition comprising an effective amount of at least one pathogen antigen and an adjuvant compound in a WOW emulsion.

A further object of the invention is a composition comprising an effective amount of at least one antigen and an adjuvant compound in a WOW emulsion for use to induce an immune response against said at least one antigen in a non-human animal.

Antigen

The term "antigen" refers to an agent that when introduced into an animal, can be recognized by the immune system of the animal and elicit an immune response. When administered to an animal, antigens generally specifically interact with an antigen recognition molecule of the immune system such as, e.g., an immunoglobulin (antibody) or a T cell antigen receptor (TCR) to elicit an immune response leading to the generation of a cell response (e.g., memory cells (e.g., memory B- and T-cells) or cytotoxic cells) and/or a humoral (antibody) response.

The invention may be used with any type of antigens such as, without limitation, whole pathogens (such as cells, viruses) or fragments or fractions thereof (such as proteins, polypeptides, peptides, nucleic acids, lipids, etc.). The pathogen may be any agent capable of infecting an animal, for example, a human, avian (e.g., chicken, turkey, duck, pigeon, etc.), canine, feline, bovine, porcine, or equine. Preferably, the antigen is an avian pathogenic agent, more preferably chicken. The antigen may be e.g., a whole pathogen, a "surface antigen" expressed naturally e.g., on the surface of a pathogen or of an infected or diseased (e.g. tumor) cell.

More particularly, the antigen may be any pathogenic, or not, microorganisms, such as viruses, bacteria, any other parasites, or antigens. These may be live, attenuated, inactivated, or killed microorganisms, either whole microorganisms or microorganisms' subunits, inactivated chimeric or recombinant microorganisms, disrupted microorganisms, mutant microorganisms, defective microorganisms, or combinations thereof. The antigen may also be or include one or more epitopes or antigenic parts of the whole microorganism structure, e.g., virus, bacteria or parasite, such as preparations of antigenic proteins from pathogens, recombinant proteins, preferably viral antigen, such as viral capsid proteins, cell wall proteins, peptides, or parts of bacterial or parasite structure, such as polysaccharides, lipopolysaccharides and glycoproteins. The antigen may also be a DNA or recombinant DNA. Antigens may be provided in a purified or an unpurified form.

When the antigen is an attenuated microorganism, such as a virus, bacterium or other pathogens, the attenuated pathogen retains immunogenic properties and is essentially devoid of pathogenic properties. Attenuation can come from natural or artificial attenuation processes such as passages in living animals or various natural media including organs, cells, embryonated eggs, etc. Artificial attenuation can also be obtained by chemical treatment, drying, aging, adaptation to low temperatures or particular conditions of culture, genetic deletions, etc.

The antigen may also comprise killed inactivated microorganisms. Preparation of inactivated viruses for vaccination is generally achieved via chemical or physical means. Chemical inactivation can be effected by treating viruses for example with enzymes, formaldehyde, β-propiolactone, Binary ethylene-imine or a derivative thereof. Inactivated virus so obtained may be neutralized or stabilized afterwards. Physical inactivation may be carried out by subjecting viruses to energy-rich radiation, such as UV-light, X-radiation or γ-radiation.

Bacteria, including spores, can be inactivated e.g., by heat, pressure and/or the use of chemical agents often referred to as bacteriocides. For example, corrosive compositions, e.g., formaldehyde and sodium hypochlorite (bleach), have been used to inactivate bacteria. Alternatively, inactivation of bacteria may be obtained by ethylene oxide exposure, g-irradiation, steam sterilization, or by using near- and supercritical carbon dioxide treatment. The bacteria may also by inactivated or rendered avirulant by genetic modification of one or several genes involved in pathogenicity. Examples of such genetic modifications are disclosed for instance in WO2012/092226.

Such attenuated or inactivated microorganisms, e.g., viruses, bacteria or other avian parasites may also be purchased from commercial sources.

The antigen may be homologous (such as chicken virus to protect chickens) or heterologous (such as turkey virus to protect chickens) types.

Vaccines or compositions of the invention may comprise a combination of live antigens, synthetic antigens, fragments or fractions thereof. The compositions may also comprise antigens from various pathogens, to provide broad immune response.

According to the present invention, the antigen may be (derived from) viruses responsible for common diseases as described by G. D. Butcher, J. P. Jacob, and F. B. Mather (PS47, Veterinary Medicine-Large Animal Clinical Sciences Department, Florida Cooperative Extension Service, Institute of Food and Agricultural Sciences, University of Florida; May 1999) such as Avian Pox, Newcastle Disease, Infectious Bronchitis, Quail Bronchitis, Lymphoid Leukosis, Marek's Disease, Infectious Bursal Disease, Infectious Laryngo tracheitis, Egg Drop Syndrome, Reovirosis, Infectious Tenosynovitis, Avian Encephalomyelitis, Swollen Head Syndrome, Turkey Rhinotracheitis or Avian Influenza, from bacteria responsible for mycoplasmosis, pasteurellosis, salmonellosis, bordetellosis, etc., and/or from other avian parasites responsible for coccidiosis, campylobacteriosis. Preferred vaccine used in the vaccine composition of the present invention comprises whole attenuated live virus strain.

Preferred antigens are or derive from cellular pathogens, particularly from bacteria or fungi such as *Actinobaccilus pleuropneumoniae, Pasteurella multocida, Streptococcus pneumonia, Streptococcus pyogenes, E. coli, Salmonella, Shigella, Yersinia, Campylobacter, Clostridium, Vibrio* and *Giardia, Entamoeba,* and *Cryptosporidium*.

In a particular embodiment, the at least one antigen comprises a bacterial cell, preferably a live, attenuated, or inactivated bacterium. Within the context of the present invention the bacterial cell can comprise whole cells, cell sub-fractions or debris or pellets thereof.

In a preferred embodiment, the bacterial cell is a *salmonella* bacterium, preferably selected from strains of *Salmonella enteritidis, Salmonella kentucky, Salmonella typhimurium, Salmonella heidelberg*, or a combination thereof. More particularly, the antigen comprises a combination of several different bacterial cells, more preferably of different strains of *Salmonella*, and/or sub-fractions thereof. In a preferred embodiment, the antigen comprises at least two different *Salmonella* cells selected from *Salmonella enteritidis, Salmonella typhimurium*, and *Salmonella kentucky*.

Adjuvant

As indicated, the invention combines a WOW formulation and an adjuvant compound. The WOW formulation and adjuvant both exert an adjuvant activity which, when combined according to the invention, surprisingly provide a synergistic effect.

Within the context of the invention the additional adjuvant is any compound that can promote or stimulate an immune response to an antigen.

Examples of adjuvants include, without limitation, proteins, polypeptides, peptides, nucleic acids (such as oligonucleotides), sugars, toxins, lipids, synthetic molecules or salts such as aluminum salts. More specific examples of adjuvants include chemical and polypeptide immunostimulants which enhance the immune system response to antigens. Such adjuvants may include for example, aluminum hydroxide, aluminum phosphate, cytokines, lymphokines, adhesion molecules, bacterial toxins, chitin derivatives and chitosan and the like.

Aluminum salts are currently used with antigens as aluminum-precipitated vaccines and as aluminum-adsorbed vaccines. As an example of an aluminum salt, aluminum hydroxide may be cited.

In a preferred embodiment, the additional adjuvant is an aluminum salt, preferably aluminum hydroxide.

In a particular embodiment, the adjuvant is an antigen-adjuvant complex, preferably in combination with a further amount of the at least one antigen as defined above. More preferably, the adjuvant is an antigen-aluminum hydroxide complex.

WOW Emulsion

Figure 1:
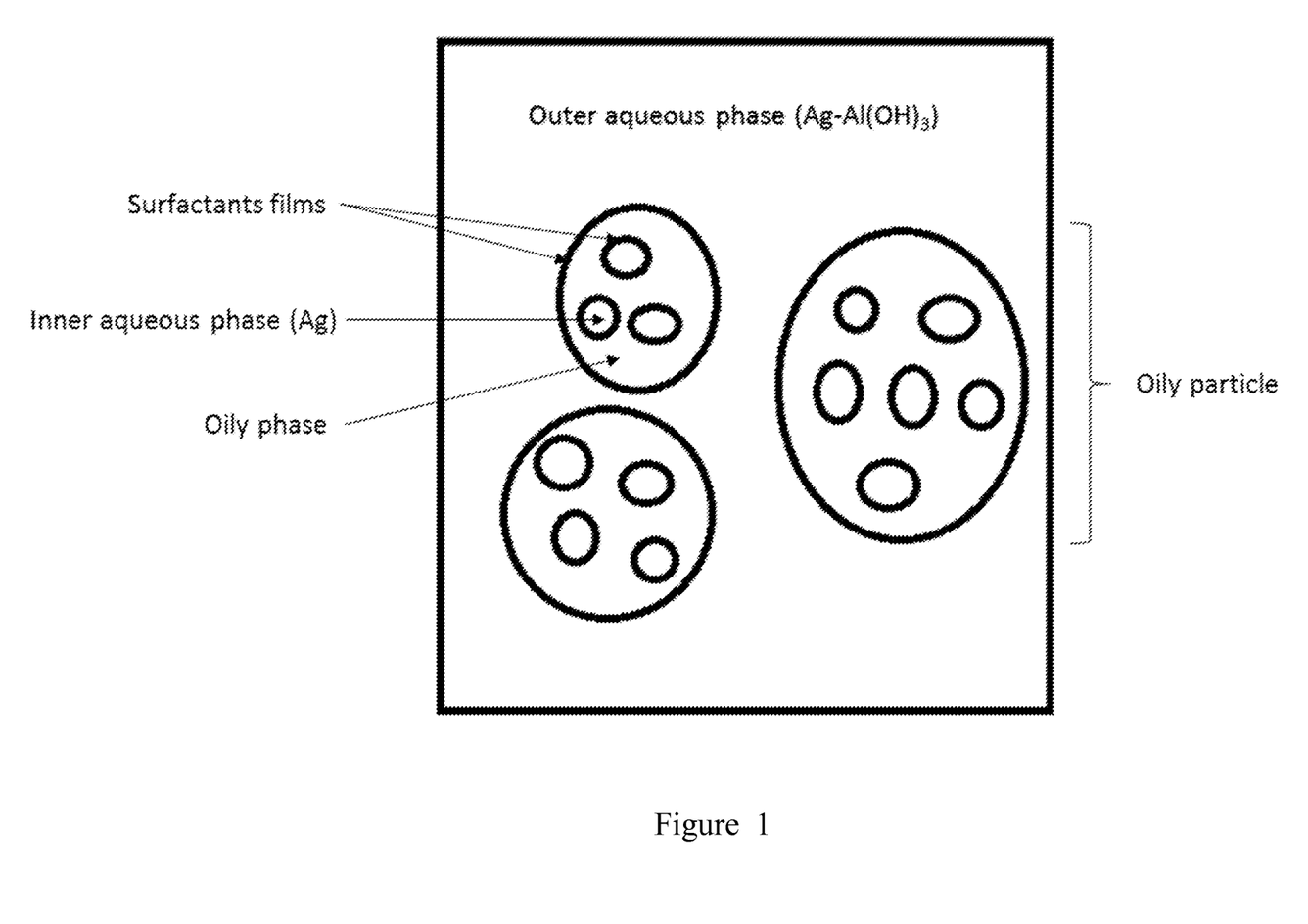
FIG. 1: Representation of a WOW emulsion.

The term "WOW" designates a Water-in-Oil-in-Water emulsion. Water-in-oil-in-water (WOW) emulsions are emulsions where small water droplets or water vesicles (inner aqueous phase) are embedded within oily particles (oily phase), dispersed in a continuous water phase (outer aqueous phase). WOW emulsions result from a primary emulsion in which an aqueous phase is added to an oily phase, followed by at least a secondary emulsion in which said oily phase is dispersed in an aqueous phase. Particular WOW emulsions or compositions of the invention, as illustrated in FIG. 1, typically comprise an inner aqueous phase corresponding to water vesicles or droplets surrounded by a first surfactant film, an oily phase surrounded by a second surfactant film, and an outer aqueous phase.

Typical WOW compositions are particulate compositions comprising water vesicles embedded within oily particles, said oily particles being dispersed in an outer aqueous phase.

Preferably, the antigen or a fraction thereof is contained in the inner aqueous phase embedded or encapsulated in the oily vesicles, and the additional adjuvant compound is in the outer aqueous phase. In a preferred embodiment, the outer aqueous phase comprises a fraction of said at least one antigen and said additional adjuvant, preferably in the form of an antigen-adjuvant complex. According to a preferred embodiment, approximately 75% of the total amount of antigen in the composition is in the oily vesicles, and approximately 25% of the total amount of antigen in the composition is in the outer aqueous phase, optionally complexed to the adjuvant compound.

The WOW emulsion may have various size/distribution characteristics. However, in a preferred embodiment, the oily particles have a size which is comprised between 1 and 40 μm, more preferably between 3 and 30 μm, even more preferably between 3 and 20 μm, most preferably between 5 and 20 μm. The size of a particle typically designates its diameter. The invention indeed shows that such range of size provides the best immunological potency upon in vivo administration.

More particularly, in preferred WOW compositions of the invention, at least 80% of the oily particles have a size below 20 µm, more preferably at least 85%, even more preferably at least 90% of the oily particles have a size below 20 µm. Furthermore, in preferred embodiments, at least 5%, preferably approximately 10% of the oily particles have a size equal to or below 10 µm, preferably a size comprised between 5 and 10 µm. Most preferred compositions of the invention have a distribution profile of oily particles such that at least 90% of the oily particles have a size less than or equal to 20 µm and at least 10% have a size below 10 µm (e.g., D10≤10 µm and D90≤20 µm). The invention shows that with such size and distribution profile, a particularly strong immune response may be generated against bacterial antigens.

Oil

Suitable oils for use in WOW emulsions of the invention include, without limitation, vegetable oils, animal oils, and mineral oils, or mixtures thereof.

Examples of vegetable oils include, without limitation, coconut oil, corn oil, cottonseed oil, olive oil, palm oil, peanut oil, rapeseed oil, canola oil, safflower oil, sesame oil, soybean oil, sunflower oil, mustard oil, lanolin oil, almond oil, argan oil, castor oil, macadamia oil, cashew oil, hazelnut oil, mongogo nut, pecan oil, pistachio nut, walnut oil, calophyllum oil, avocado oil, soya oil, jojoba oil or mixtures thereof.

Examples of animal oils include, without limitation, fish oil, turtle oil, mink oil, chicken fat oil, whale oil, sperm whale oil, seal oil, cod liver oil, emu oil, hydrogenated squalene (or perhydrosqualene) or mixture(s) thereof.

Examples of mineral oils include, without limitation paraffin oil such as paraffin and isoparaffins, petroleum jelly oil, Drakeol, or Mineral Oil Light No. 5.

In a particular embodiment, the WOW emulsion and oily particles of the invention comprise one or several oils, preferably selected from vegetable, animal and mineral oils or mixture thereof. Preferably the WOW emulsion and oily particles comprise at least a mineral oil.

Surfactant

In a preferred embodiment, the WOW emulsions of the invention further contain at least one surfactant.

The surfactant(s) are typically selected, or combined, or used under conditions providing a proper Hydrophilic-Lipophilic Balance (HLB) to the formulation. The HLB of a surfactant or of a combination of surfactants is a measure of the degree to which it is hydrophilic or lipophilic, determined by calculating values for the different regions of the molecules as described by Griffin (Journal of the Society of Cosmetic Chemists, 1949, 1(5), 311-26 and Journal of the Society of Cosmetic Chemists, 1954, 5(4), 249-56).

Most preferably, the surfactant or combination of surfactants used in the first emulsion has a low HLB value (typically between 4 and 7, preferably of about 6.0), and the surfactant or combination of surfactants used in the second emulsion has a high HLB value (typically between 7 and 15, preferably about 10.5).

Examples of surfactant used in emulsion vaccines include, without limitation, sorbitan monooleate (Span 80), polyoxyethylene sorbitan monooleate (Tween 80), sorbitan sesquioleate (Span 83), Lecithin, and mannide monooleate, or mixtures thereof.

Preferably, WOW emulsions of the invention comprise at least one surfactant selected from polyoxyethylene sorbitan monooleate and sorbitan monooleate. More preferably, the surfactant used in the first WO emulsion is a combination of Span 80 and Tween 80, and the surfactant used in the second OW emulsion is Tween 80.

Salts

Vaccines and compositions of the invention optionally further comprise one or several salts. The addition of a salt can inhibit osmosis of water into the oily particles and further stabilize the oily particles.

Examples of such salts include, without limitation, sodium chloride, magnesium chloride, sodium sulfate or magnesium sulfate. In a particular embodiment, the salt is sodium chloride.

Preservatives

The compositions of the invention may further comprise one or more preservatives that are acceptable in the veterinary field. Without limitation, examples of suitable preservatives include:

acids, such as benzoic acid, sorbic acids and sodium or potassium salts thereof;

esters, such as methylparaben, ethylparaben and propylaparaben;

alcohols, such as chlorobutanol, benzyl alcohol, phenyl ethyl alcohol, phenoxyethanol, phenols such as chlorocresol and o-phenyl phenol;

mercurial compounds such as thimerosal, nitromersol, phenylmercuric nitrate and phenylmercuric acetate;

quaternary ammonium compounds such as benalkonium chloride and cetyl pyridium chloride.

In a preferred embodiment, the preservative is a thimerosal solution, and typically a 10% thimerosal solution.

Method of Preparation

The compositions of the invention may be produced using techniques generally known per se in the art. Preferably, however, the method comprises a first step of forming the WOW emulsion and a second step of mixing said WOW emulsion with an additional adjuvant compound.

More particularly, the vaccines of the invention are obtainable by a process comprising the steps of:

a) emulsifying a solution of said at least one antigen in an oil base, thereby forming a water-in-oil (WO) emulsion, b) adding said WO emulsion to a dispersal phase, thereby forming a WOW emulsion and emulsifying said WOW emulsion, and c) mixing said WOW emulsion with the additional adjuvant, preferably in combination with a further amount of said at least one antigen.

A further object of the invention therefore resides in a process for the preparation of a composition comprising at least one antigen and an additional adjuvant, the process comprising the steps of:

a) emulsifying a solution of said at least one antigen in an oil base, thereby forming a water-in-oil (WO) emulsion, b) adding said WO emulsion to a dispersal phase, thereby forming a WOW emulsion and emulsifying said WOW emulsion, and c) mixing said WOW emulsion with the additional adjuvant, preferably in combination with a further amount of said at least one antigen.

In a particular embodiment, the oil base at step a) comprises one or several oils and at least one surfactant as defined above. Preferably, the oil base comprises a mineral oil and a combination of Span 80 and Tween 80. More preferably the surfactant or mixture of surfactants provides a HLB between 4 and 7, preferably of about 6.0.

In a further particular embodiment, the dispersal phase at step b) comprises deionized water and at least one surfactant, preferably Tween 80. In a particular embodiment, the dispersal phase further comprises a salt and/or a preservative as defined above. Preferably, the dispersal phase comprises deionized water, sodium chloride, Tween 80, and thimerosal solution. Particularly the surfactant (e.g., Tween 80) or mixture of surfactants provides a HLB between 7 and 15, preferably of about 10.5.

In another particular embodiment, the additional adjuvant in step c) is such as defined above. Preferably, the additional adjuvant is or comprises aluminum hydroxide, preferably in combination with a further amount of said at least one antigen.

The emulsification steps may be run through a multistage emulsifier set in which parameters of circulations are determined to obtain oily particles with a predetermined size.

In a particular embodiment, the solution of said at least one antigen in an oil base is emulsified at a very high revolution per minute (rpm), preferably between 15000 and 30000 rpm, more preferably between 20000 and 25000 rpm, typically of about 22000 rpm, for at least one circulation, preferably for three circulations. The emulsion is then added to said dispersal phase and emulsified at low rpm, preferably between 1000 and 6000 rpm, more preferably between 2000 and 5000 rpm, typically of about 3000 rpm for at least one circulation, preferably for two circulations, more preferably for three circulations. Optionally, an additional circulation is performed at a middle rpm, preferably between 5000 and 15000 rpm, more preferably between 8000 and 12000 rpm, typically of about 10000 rpm.

Such particular process conditions allow to obtain oily particles loaded with the at least one antigen with a size distribution profile as defined above, and preferably with about 10% of the particles (D10) having a size <10 μm, preferably between 5 and 10 μm, and about 90% of the particles (D90) having a size <20 μm.

Such size distribution profile of oily particles loaded with at least one said antigen provides a stable WOW emulsion that is less viscous than traditional water-in-oil emulsions, is easily syringable, and highly immunogenic.

Following emulsion steps a) and b), the compositions of the invention are obtained by mixing one or several additional adjuvant compound(s) with the WOW emulsion, preferably in combination with a further amount of said at least antigen.

Accordingly, a preferred method for preparing a composition of the invention comprises:

a) emulsifying a solution of said at least one antigen in an oil base through a multistage emulsifier set at about 22000 rpm for three circulations, thereby forming a water-in-oil (WO) emulsion, b) emulsifying said WO emulsion in a dispersal phase through a multistage emulsifier set at about 3000 rpm for three circulations and at about 10000 rpm for one additional circulation, thereby forming a WOW emulsion, and c) mixing the additional adjuvant, preferably aluminum hydroxide, with said WOW emulsion, preferably in combination with a further amount of said at least one antigen.

In a more preferred embodiment, step a) is carried at HLB about 6.0 and step b) is carried at HLB about 10.5.

Preferred Compositions

Preferred compositions and vaccines of the invention are described below. These compositions can induce strong and persistent immune protection in vivo, including within internal organs, allowing effective protection of e.g., non-human animals against various diseases.

A particular composition of the invention comprises bacterial antigens combined with an adjuvant compound in a WOW emulsion having particle size comprised between 1 and 30 μm.

A further particular composition of the invention comprises bacterial antigens combined with an adjuvant compound in a WOW emulsion having particle size comprised between 1 and 30 μm, wherein the bacterial antigens comprise whole attenuated cells.

A further particular composition of the invention comprises *Salmonella* antigens combined with an adjuvant compound in a WOW emulsion having particle size comprised between 1 and 30 μm.

A further particular composition of the invention comprises *Salmonella* antigens combined with an adjuvant compound in a WOW emulsion having particle size comprised between 1 and 30 μm, the *Salmonella* antigens comprising whole *Salmonella* cells, optionally attenuated, preferably a mixture of at least two types of *Salmonella* cells selected from ST, SE and SK.

The compositions of the present invention preferably comprise an effective amount of antigen, e.g., a quantity of the antigen that is sufficient (upon a single or repeated administration) to induce an immune response in an animal. The effective amount of antigen may be adjusted by the skilled artisan depending on the antigen, formulation and contemplated use. The amount of antigen in the composition may be assessed by various methods such as the weight, biological activity, and/or density. In a typical embodiment, the effective amount is an amount at which the composition has a total $OD_{600}$/ml superior to 4, preferably superior to 5, typically comprised between 4 and 12, preferably between 5 and 8, more preferably between 5 and 6.5. Furthermore, since the antigen may be contained in the oily particles as well as in the outer aqueous phase, it is preferred that at least 60% of the total amount of antigen in a composition of the invention is contained in the oily particles, most preferably between approximately 60-75%, the remaining 40-25% being located in the outer aqueous phase.

In this regard, a further particular object of the invention is a vaccine or immunogenic composition comprising whole bacterial cells in a WOW emulsion, wherein at least 90% of the oily particles in the WOW emulsion have a size below 20 μm, the composition has an $OD_{600}$/ml superior to 4, and at least 60% of the cells in the composition are contained in said oily particles. In a further preferred embodiment, the compositions of the invention comprise whole inactivated or attenuated bacterial cells in a WOW emulsion, wherein at least 90% of the oily particles in the WOW emulsion have a size below 20 μm and at least 5% have a size below 10 μm, the composition has an $OD_{600}$/ml superior to 5, and 60-75% of the cells in the composition are contained in said oily particles. In a preferred embodiment, these compositions further contain an additional adjuvant compound, which is typically in the outer aqueous phase.

Preferred compositions of the invention further comprise a surfactant, a salt and a preservative.

Application

The vaccines and compositions of the invention may be used to deliver an effective amount of said at least one antigen in an animal.

More particularly, the vaccines of the invention may be used to induce an immune response against at least one antigen as defined above in an animal.

As illustrated in the examples, the vaccines of the invention comprising a dual adjuvant system cause improved protection against pathogenic infection in several organs such as liver, spleen, and cecum. Furthermore, as illustrated, the effect is much stronger than that observed with prior art vaccines, illustrating a synergistic effect of the WOW and adjuvant compound.

Accordingly, a further object of the invention relates to the use of a vaccine or composition as defined above for treating and/or preventing an infection in an animal, preferably a bacterial infection.

A further object of the invention is a method for treating and/or preventing an infection in an animal, preferably a bacterial infection, comprising administering to the animal a vaccine or composition as defined above.

In a particular embodiment, the bacterial infection is a *salmonella* infection, preferably *Salmonella enteritidis* infection, *Salmonella kentucky* infection, *Salmonella typhimurium* infection or *Salmonella heidelberg* infection.

The compositions and vaccines of the invention may be administered by any conventional route, such as by systemic administration, preferably by intramuscular administration, subcutaneous administration, intravenous administration, intraperitoneal administration, nasal application, ocular administration, more preferably by injection.

The invention is particularly suitable for treating non-human animals, particularly poultry (e.g., chickens), bovines, ovines or porcines. Particularly, the animal is a chicken.

In a particular embodiment, the vaccine of the invention is administered to an animal having a low tolerance to conventional vaccines in a water-in-oil (WO) emulsion.

Further aspect and advantages of the invention will be disclosed in the following experimental section, which illustrates the claimed invention.

EXAMPLES

A. Production of Vaccine a Comprising Bacterial Antigens

The bacterial antigen was a combination of *Salmonella enteritidis-kentucky-typhimurium* Bacterin product produced at the minimum antigen concentration. The placebo was produced utilizing the same process as the vaccine, containing all adjuvants and other components, without addition of the *Salmonella* Antigen. Antigenic formulation for each 0.50 ml dose of *Salmonella enteritidis-kentucky-typhimurium* Bacterin and Placebo are illustrated in the Table 1 below.

TABLE 1

| | A: *Salmonella Enteritidis-*Kentucky-*Typhimurium* Bacterin | | | Placebo | | |
|---|---|---|---|---|---|---|
| Fraction | OD/ml | Volume added (ml) | OD/fraction | Concentration OD/ml | Volume (ml) | Calculated OD |
| *Salmonella enteritidis* | 66.07 | 302.71 | 20000 | 0 | 0 | 0 |
| *Salmonella* kentucky | 65.28 | 306.37 | 20000 | 0 | 0 | 0 |
| *Salmonella typhimurium* | 91.85 | 217.75 | 20000 | 0 | 0 | 0 |
| saline (substitute for antigen) | NA[1] | NA | NA | NA | 414 | NA |
| dispersal phase solution[2] | NA | 5008 | NA | NA | 2503 | NA |
| oil base adjuvant[3] | NA | 3222 | NA | NA | 1612 | NA |
| aluminum hydroxide | NA | 942.72 | NA | NA | 471 | NA |
| | Total OD = 60000 | | | Total OD = 0 | | |
| | Total Volume = 10000 ml | | | Total Volume = 5000 ml | | |
| | Total OD/ml = 6.00 | | | Final OD/ml = 0 | | |
| | Total OD/0.5 ml dose = 3.00 | | | | | |
| | SE = 1.00 OD/0.5 ml dose | | | Final OD/0.5 ml dose = 0 | | |
| | SK = 1.00 OD/0.5 ml dose | | | | | |
| | ST = 1.00 OD/0.5 ml dose | | | | | |

[1]NA = Not applicable

[2]The dispersal phase was prepared by combining 0.85% sodium chloride, Tween 80, and Thimerosal.

[3]Oil adjuvant was prepared by combining mineral oil, Span 80 and Tween 80 such that the hydrophilic - lipophilic balance was at 6.0 and the remaining Tween was added to the dispersal phase to give a final hydrophilic - lipophilic balance of 10.5.

The vaccine was produced as follows:

Step I:

The aluminum hydroxide-antigen complex was prepared by combining 942 ml of aluminum hydroxide with 206 ml of pooled antigen (25% of pooled antigen). The complex was mixed for at least four hours at room temperature and then stored at 2-7° C. until use.

Step II:

3222 ml of oil base was circulated through the emulsifier at approximately 22,000 revolutions per minute (rpm) and 620 ml pooled antigen (75% of pooled antigen) was slowly added just prior to the entry of the emulsifier. After the antigen was added, the solution was emulsified for three circulations at 22,000 rpm. This created a water-in-oil (WO) emulsion.

Step III:

The WO emulsion was then slowly added to 5008 ml of dispersal phase (0.85% sodium chloride, Tween 80, and Thimerosal) with vigorous mixing, and allowed to mix for one hour. This created a water-in-oil-in-water (WOW) emulsion.

Step IV:

The particle size of the WOW emulsion was reduced by emulsification at 3,000 rpm for three circulations followed by one circulation at 10,000 rpm. The D10 and D90 particle size range was 8.6 and 12.2 micrometer, respectively.

Step V:

1148 ml of the aluminum hydroxide-antigen complex was then mixed into the WOW emulsion and allowed to mix for at least one hour at room temperature before filling.

B. Production of Vaccine B Comprising Bacterial Antigens

The bacterial antigen was a combination of *Salmonella enteritidis-kentucky-typhimurium* Bacterin product produced at the minimum antigen concentration. The placebo was produced utilizing the same process as the vaccine, containing all adjuvants and other components, without addition of the *Salmonella* Antigen. Antigenic formulation for each 0.50 ml dose of *Salmonella enteritidis-kentucky-typhimurium* Bacterin and Placebo are illustrated in the Table 2 below.

TABLE 2

| Fraction | B: Salmonella Enteritidis-Kentucky-Typhimurium Bacterin | | | Placebo | | |
|---|---|---|---|---|---|---|
| | OD/ml | Volume added (ml) | OD$_{600}$/fraction | Concentration OD/ml | Volume (ml) | Calculated OD$_{600}$ |
| Salmonella enteritidis | 37.46 | 534 | 20003 | 0 | 0 | 0 |
| Salmonella kentucky | 34.62 | 577 | 19975 | 0 | 0 | 0 |
| Salmonella typhimurium | 40.95 | 327 | 13390 | 0 | 0 | 0 |
| saline (substitute for antigen) | NA[1] | NA | NA | NA | 288 | NA |
| dispersal phase solution[2] | NA | 4394 | NA | NA | 880 | NA |
| oil base adjuvant[3] | NA | 3223 | NA | NA | 644 | NA |
| aluminum hydroxide | NA | 942 | NA | NA | 190 | NA |
| | Total OD = 53368 | | | Total OD = 0 | | |
| | Total Volume = 9997 ml | | | Total Volume = 2002 ml | | |
| | Total OD/ml = 5.34 | | | Final OD/ml = 0 | | |
| | Total OD/0.5 ml dose = 2.67 | | | | | |
| | SE = 1.00 OD/0.5 ml dose | | | Final OD/0.5 ml dose = 0 | | |
| | SK = 1.00 OD/0.5 ml dose | | | | | |
| | ST = 0.67 OD/0.5 ml dose | | | | | |

[1]NA = Not applicable
[2]The dispersal phase was prepared by combining 0.85% sodium chloride, Tween 80, and Thimerosal.
[3]Oil adjuvant was prepared by combining mineral oil, Span 80 and Tween 80 such that the hydrophilic - lipophilic balance was at 6.0 and the remaining Tween was added to the dispersal phase to give a final hydrophilic - lipophilic balance of 10.5.

The vaccine was produced as follows:
Step I:
The aluminum hydroxide-antigen complex was prepared by combining 943 ml of aluminum hydroxide with 360 ml of pooled antigen (25% of pooled antigen). The complex was mixed for at least four hours at room temperature and then stored at 2-7° C. until use.
Step II:
3223 ml of oil base was circulated through the emulsifier at approximately 22,000 revolutions per minute (rpm) and 1079 ml pooled antigen (75% of pooled antigen) was slowly added just prior to the entry of the emulsifier. After the antigen was added, the solution was emulsified for three circulations at 22,000 rpm. This created a water-in-oil (WO) emulsion.
Step III:
The WO emulsion was then slowly added to 4394 ml of dispersal phase (0.85% sodium chloride, Tween 80, and Thimerosal) with vigorous mixing, and allowed to mix for one hour. This created a water-in-oil-in-water (WOW) emulsion.
Step IV:
The particle size of the WOW emulsion was reduced by emulsification at 3,000 rpm for three circulations followed by one circulation at 10,000 rpm. The D10 and D90 particle size range was 9.3 and 12.6 micrometer, respectively.
Step V:
1300 ml of the aluminum hydroxide-antigen complex was then mixed into the WOW emulsion and allowed to mix for at least two hours at room temperature before filling.
C. Effective Protection Against Salmonella Bacteria
Materials
Vaccines 1-4 are prepared for comparative evaluation.
Vaccine 1 of the invention comprises a dual adjuvant system (WOW+Ag—Al(OH)$_3$).
Vaccine 2 comprises Ag—Al(OH)$_3$ adjuvant but is not a WOW.
Vaccine 3 comprises a WOW emulsion but no additional adjuvant compound.
Vaccine 4 comprises a WOW emulsion and Al(OH)$_3$ and no antigen (Placebo).

Vaccines No. 2-4 were prepared by standard procedures for comparative tests.
All vaccines (but not placebo) contained same amount of antigen.
Method
Chicken are vaccinated at 4 and 8 weeks of age and challenge at 12 weeks of age. Necroscopy is performed 7 days post challenge at 13 weeks of age.
Results
The results are presented in Table 3 below. As can be seen from the right end column, while vaccine 1 prevented Salmonella infection (0.002), vaccines 2-4 were very ineffective and essentially did not prevent bacterial infection.

TABLE 3

| No. | Vaccine | Type | Liver | Spleen | L/S | All |
|---|---|---|---|---|---|---|
| 1 | Ag-in-oil + Ag—Al(OH)$_3$ | WOW | 0.001 | <0.001 | <0.001 | 0.002 |
| 2 | Ag—Al(OH)$_3$ | OW | 1.000 | 0.333 | 0.333 | 1.000 |
| 3 | Ag-in-oil | WOW | 0.226 | 1.000 | 1.000 | 1.000 |
| 4[1] | Al(OH)$_3$ (placebo) | WOW | 81% | 94% | 94% | 94% |

[1]Percent of controls that were positive for reisolation of the challenge strain from the tissue.

As can be seen, vaccine 1 comprising the dual adjuvant system of the invention gave remarkable protection in all of the tested target tissues.
Vaccine 2, a simple OW emulsion, was not effective in particular in liver (reisolation=100%); and Vaccine 3, devoid of adjuvant compound, was also not effective for all tissues (reisolation=100%).
Therefore the inventors have surprisingly showed an improved efficacy for vaccines of the invention for preventing bacterial infection. The effect is remarkable in all tested tissues, and synergistic since it is much more potent than mono-adjuvanted comparative vaccines 2 and 3.
D: Vaccines of the invention effectively protect against bacterial infection in vivo
Materials and Methods
Animals
Specific pathogen-free chickens from Charles River were used in this study. At one day of age, the chicks were transported to a Rural Technologies, Inc. facility located in South Dakota State University Brookings, S. Dak. All chickens remained in the same room (commingled) for the duration of the study. To confirm the negative *salmonella* status of the chickens, cloacal swabs were collected from individual chickens at 12 and 24 weeks of age, and tested for reisolation of *salmonella*.

Challenge Organisms

Chickens in all treatment groups were challenged with a heterologous SE (*Salmonella enteritidis*), SK (*Salmonella kentucky*), ST (*Salmonella typhimirium*) or SH (*Salmonella heidelberg*) challenge strain. The challenge dose was determined by a viable count assay.

Methods

Specific pathogen-free chickens at 14 weeks of age were randomly divided into three treatment groups and vaccinated. One group was vaccinated with *Salmonella enteritidis-kentucky-typhimurium* Bacterin (Vaccine A) using a 0.5 ml IM (Intramuscular) dose. The second group was also vaccinated with 0.5 ml of vaccine A, administered by SQ (Sub-cutaneous) route. The third group was administered the placebo using a 0.5 ml dose; half of these chickens were administered the placebo by the SQ route and half by the IM route. At 18 weeks of age, the chickens were administered another 0.5 ml dose of the vaccine or placebo by the same route. Eight weeks after the second vaccination, when the chickens were 26 weeks of age, all chickens were challenged with a virulent heterologous SE, SK ST, or SH challenge strain. One week after challenge, the chickens were necropsied, and the cecum, liver/spleen or ovaries were collected from each chicken and tested for SE, SK, ST or SH colonization. The reisolation results were used to complete prevented fraction evaluation to determine whether or not the bacterin aided in the reduction of colonization of SE, SK, ST or SH in the cecum, liver/spleen, or ovaries. Vaccination, observation, challenge and reisolation were conducted at RTI (Rural Technologies, Inc).

Screening for *Salmonella*

1. Pre Vaccination

Twenty (20) chickens were euthanized and necropsied at six weeks of age. The liver, spleen and cecum were sampled and tested as described below in the "Detection of Tissue Colonization" section. Cloacal swabs were taken from all chickens at 13 weeks of age. Each of these chickens was swabbed with a pre-moistened swab and five bird swabs were pooled into a tube containing 10 ml of tetrathionate brilliant green enrichment broth (TTBG). The tubes were incubated at 42° C. for 48 hours. After 24 hours incubation, a 10-microliter aliquot of each TTBG broth culture was streaked onto xylose lysine agar plates containing tergitol 4 (XLT4) and incubated at 37° C. for 48 hours. Following 24 hours incubation, the XLT4 plates were examined for the presence of black or black-centered colonies that are typical for *salmonella* (Difco Manual, 1998). Broth cultures that were negative for colonies typical of *salmonella* after being streaked onto XLT4 for the first time, were re-streaked onto XLT4 at 48 hours post incubation and the plates evaluated 24 and 48 hours later. Samples that were negative from 24- and 48-hour sampling were then tested by Delayed Secondary Enrichment (DSE). Briefly, the TTBG tubes were set at room temperature (20-25° C.) for 5-7 days before a 1-ml sample was transferred to 9 ml of fresh TTBG. These tubes were then incubated for 24 hours at 37° C., inoculated onto XLT4 plates, and the plates were incubated 48 hours at 37° C. Following 48 hours incubation, the XLT4 plates were examined for the presence of black or black-centered colonies that are typical for *salmonella* (Difco Manual, 1998).

2. Post Vaccination/Pre Challenge

Two weeks prior to challenge when the birds were 24 weeks of age, cloacal swabs were taken from all birds to be challenged and screened for the presence of *salmonella* as described above.

Method of Challenge

At eight weeks post second vaccination when the chickens were 26 weeks of age, all birds were challenged with a 0.5 ml of a freshly grown virulent heterologous culture of SE, SK, ST or SH diluted to contain between $1 \times 10^3$ and $1 \times 10^7$ colony forming units (CFU) by oral or intramuscular administration. To prepare the challenge, frozen seed was thawed, 1 ml was transferred into 250 ml soy peptone broth and incubated at 37° C. for 6 hours. One (1) ml of the 6-hour culture was added to a predetermined volume of phosphate buffered saline (PBS) for the oral or intramuscular challenge. This challenge preparation was serially diluted and plated to obtain the viable count at challenge.

Detection of Tissue Colonization

At seven days post challenge (dpc), each bird was necropsied. The liver, spleen, ovaries, and cecal pouches with contents were sampled and tested for challenge strain colonization as a direct method of demonstrating a protective response. The entire spleen and approximately 1 g of liver were placed in the same tissue grinder, 20 ml TTBG was added to each grinder, the tissues were minced and then incubated at 37° C. for 48 hours. Ovaries including ova were placed in a Whirl-Pak bag, macerated by hand, weighed, transferred to TTBG at a 1:10 w/v ratio of tissue to media and then incubated at 37° C. for 48 hours. Approximately 1 gram of each cecal pouch with contents was placed in a disposable sterile tissue grinder with a lid, 20 ml TTBG broth was added, the tissue was minced and the tissue grinder containing the sample was incubated at 42° C. for 48 hours. After 24 hours incubation, an aliquot of each TTBG broth culture was streaked onto XLT4 agar and incubated at 37° C. for 24 hours. The TTBG broth cultures were returned to incubation at the appropriate temperature for further growth. Following 24 hour incubation, the XLT4 plates were examined for the presence of black or black-centered colonies that are typical for *salmonella* (Difco Manual, 1998). Broth cultures that were negative for colonies typical of *salmonella* on the XLT4 the first time were re-streaked a second time at 48 hours post incubation onto new XLT4 plates, incubated at 37° C. for 24 hours and evaluated at that time. For confirmation tests, bacterial colonies that were typical for *salmonella* on XLT4 plates were inoculated onto three different agars: triple sugar iron agar (TSI), lysine iron agar (LIA), and veal agar, and incubated for 24 h at 37° C. If an isolate gave a typical reaction for *salmonella* on TSI and LIA (Difco Manual, 1998), then colonies of that isolate were picked from the veal agar plate for agglutination in single factor species-specific *Salmonella* O single factor antiserum to confirm *Salmonella* group, and in *Salmonella* H:g,m antiserum to confirm *Salmonella* serotype of the challenge organism.

All tissue samples from all treatment groups that were negative for primary enrichments were tested by delayed secondary enrichments (DSE). Briefly, the TTBG cultures were stored at room temperature (20-25° C.) following the initial 48 hour incubation period. Six (6) days after being moved to room temperature, the cultures were enriched in fresh TTBG broth by adding 1 ml of the culture to 9 ml of fresh TTBG. The samples were then incubated at 42° C. After 24 hours incubation, an aliquot of each TTBG broth culture was streaked onto XLT4 agar and incubated at 37° C. for 48 hours. Following 24 and 48 hours incubation, the XLT4 plates were examined for the presence of black or black-centered colonies that are typical for *salmonella* (Difco Manual, 1998).

Estimator

The IM and SQ vaccinated groups that received bacterin containing antigen were each compared to the placebo-vaccinated group for colonization of the challenge strain in the internal organs, cecum, liver/spleen, ovaries and reproductive tract following challenge. Efficacy of the bacterin for each treatment group was statistically evaluated by calculating the prevented fraction (complement of the risk ratio) for colonization of SE, SK, ST or SH in the internal organs, reproductive tract and/or intestines.

Statistics

The prevented fraction (complement of the risk ratio) was calculated according to the formula $PF=1-p_v/p_c$, where $p_v$ and $p_c$ are the affected fractions of vaccinates and controls, respectively. As stated in the protocol, the control group contains all chickens that received the placebo, regardless of IM or SQ administration. All analyses were performed on all available data using the SAS® System, version 9.3 (code was provided by APHIS), and R 2.13.0.

Results

Screening for *Salmonella*

All tissues samples from six-week old chickens and all cloacal samples from 24-week-old chickens were negative, indicating that the chickens were free of *Salmonella* prior to vaccination and prior to challenge.

Safety Observations

Chickens were observed daily for any vaccine-related adverse reactions and for mortality. No adverse vaccine reaction or incidence of mortality was observed in any chicken.

1. Protection Against *Salmonella enteritidis* (SE) Infection

The results are illustrated in the following table 4 and FIGS. 2A and 2B.

TABLE 4

Frequency (%) of reisolation, prevented fraction and 95% Confidence Limits with vaccine A.

| Tissue | Comparison | Proportion Positive | Lower 95% CL[1] | Prevented Fraction | Upper 95% CL[1] |
|---|---|---|---|---|---|
| liver/spleen | IM | 14/56 (25.0%) | 0.553 | 0.708 | 0.847 |
| | placebo | 48/56 (85.7%) | NA | NA | NA |
| | SQ | 38/63[2] (60%) | 0.122 | 0.298 | 0.438 |
| | Placebo | 55/64 (86.0%) | NA | NA | NA |
| cecum | IM | 11/52 (21%) | 0.235 | 0.577 | 0.786 |
| | placebo | 25/50 (50%) | NA | NA | NA |
| | SQ | 11/51 (22%) | 0.191 | 0.569 | 0.781 |
| | placebo | 25/50 (50%) | NA | NA | NA |
| ovaries | IM | 3/54 (5.6%) | 0.767 | 0.914 | 0.989 |
| | placebo | 36/56 (64.3%) | NA | NA | NA |
| | SQ | 19/62[3] (30.6%) | 0.378 | 0.584 | 0.722 |
| | placebo | 47/64 (73%) | NA | NA | NA |

[1]CL = confidence limit
[2]One chicken died one day post challenge and was excluded from statistics
[3]Two chicken did not have developing ovaries and was excluded from statistics
IM: intramuscular
SQ: subcutaneous
N/A: Not applicable The results show that:

Vaccine A administered by the SQ route was effective in reducing and preventing SE colonization of all tested internal organs such as liver/spleen, cecum and ovaries.

Particularly a prevented fraction greater than 0.5 was obtained in cecum and ovaries meaning that the vaccine treatment improved more than 50% (PF=0.569 and PF=0.584) the protection SE efficacy in such internal organs.

Figure 2A:
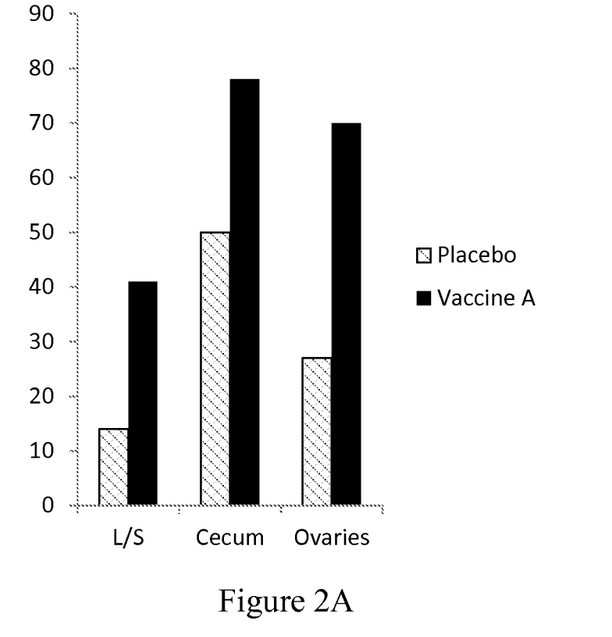
FIGS. 2A-2B: % protection against *Salmonella enteritidis* (SE) in chickens treated with vaccine A by subcutaneous route (SQ, FIG. 2A) and by intramuscular route (IM, FIG. 2B).
Figure 2B:
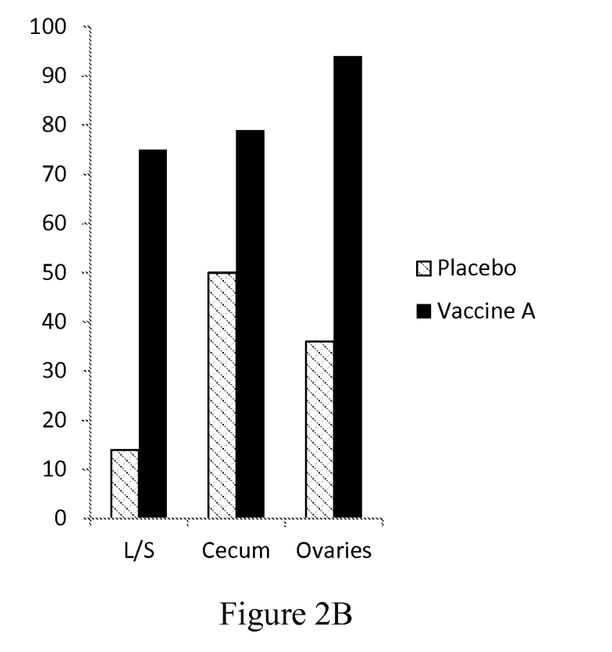

These results are also illustrated in FIG. 2A in which a protection SE efficacy greater than 70% is obtained in cecum (78%) and in ovaries (70%).

An administration of vaccine A by the IM route was even more effective in the reduction of SE colonization of all internal organs as liver/spleen, cecum and ovaries (Table 3: PF >0.7 for liver/spleen and ovaries and FIG. 2B: protection SE efficacy >75% for liver/spleen, cecum and ovaries).

The lower 95% confidence levels for all the internal organs were greater than 0 for both SQ and IM routes, which is statistically significant evidence that vaccination of chickens with vaccine A administered by the SQ and IM route was effective in reducing SE challenge strain colonization of the internal organs.

2. Protection Against *Salmonella typhimurium* (ST) Infection

Figure 3A:
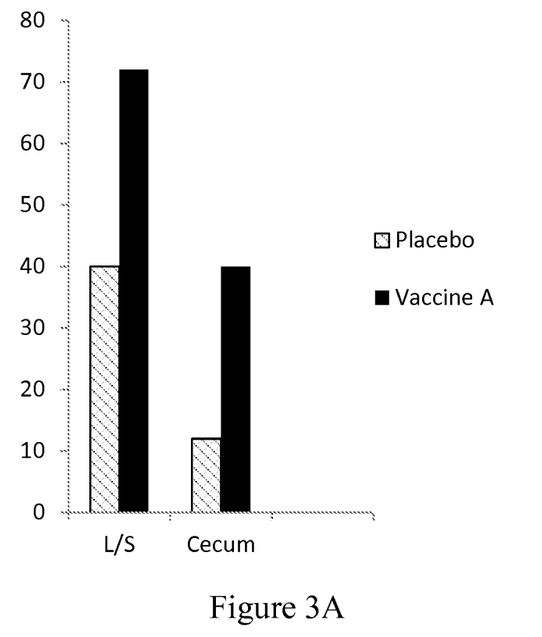
FIGS. 3A-3B: % protection against *Salmonella typhimurium* (ST) in chickens treated with vaccine A by subcutaneous route (SQ, FIG. 3A) and by intramuscular route (IM, FIG. 3B).
Figure 3B:
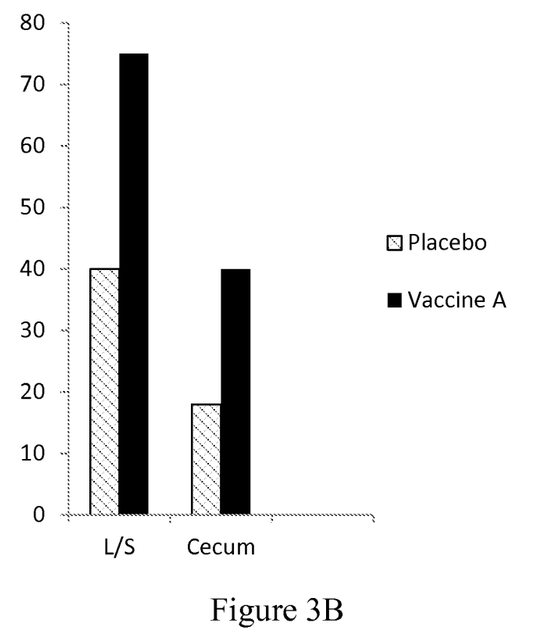

The results are illustrated in the following table 5 and FIGS. 3A and 3B.

TABLE 5

Frequency (%) of reisolation, prevented fraction and 95% Confidence Limits with vaccine A.

| Tissue | Comparison | Proportion Positive | Lower 95% CL[1] | Prevented Fraction | Upper 95% CL[1] |
|---|---|---|---|---|---|
| liver/spleen | IM | 18/71 (31%) | 0342 | 0.575 | 0.726 |
| | placebo | 43/73 (58.9%) | N/A | N/A | N/A |
| | SQ | 21/74 (28.4%) | 0.276 | 0.519 | 0.681 |
| cecum | placebo | 60/73 (82.7%) | N/A | N/A | N/A |
| | SQ | 44/74 (59.5%) | 0.101 | 0.275 | 0.416 |
| | IM | 43/71 (60.6%) | 0.085 | 0.262 | 0.406 |

[1]CL = confidence limit
IM: intramuscular
SQ: subcutaneous
N/A: Not applicable

The results show that:

Vaccine A administered by the SQ or IM route was effective in reducing and preventing ST colonization of liver/spleen and cecum. Particularly, a prevented fraction greater than 0.5 was obtained in liver/spleen, meaning an improved protection efficacy in such internal organs. FIGS. 3A and 3B also illustrate an improved protection efficacy for the both SQ and IM routes in liver/spleen (protection ST efficacy >70%) and in cecum (protection ST efficacy of 40%).

3. Protection Against *Salmonella kentucky* (SK) Infection

Figure 4:
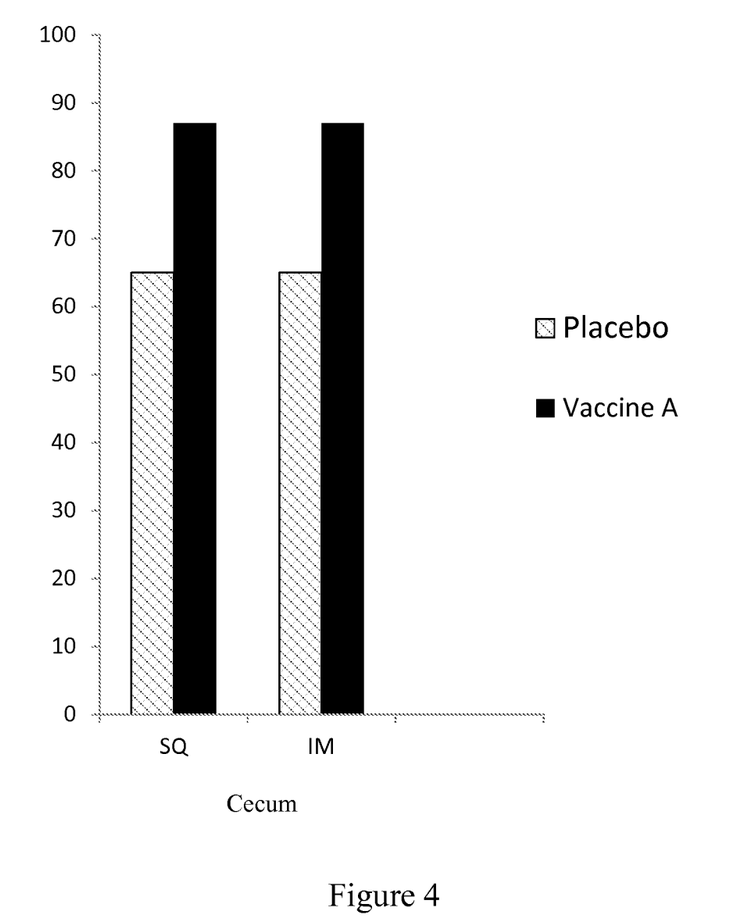
FIG. 4: % protection against *Salmonella kentucky* (SK) in chickens treated with vaccine A by subcutaneous and intramuscular route.

The results are illustrated in the following table 6 and FIG. 4.

TABLE 6

Frequency (%) of reisolation, prevented fraction and 95% Confidence Limits with vaccine A for cecum.

| Treatment | No. Positive/Total | Proportion Positive | Lower 95% CL[1] | Prevented Fraction | Upper 95% CL[1] |
|---|---|---|---|---|---|
| vaccine (IM) | 7/55[3] | 12.7% | 0.167 | 0.64 | 0.789 |
| placebo | 20/57 | 35.1% | N/A | N/A | N/A |
| vaccine (SQ) | 7/55[4] | 12.7% | 0.0.167 | 0.641 | 0.789 |

[1]CL = confidence limit
[2]One chicken died one day post challenge and was excluded from statistics
[3]Two chicken died of septicemia prior to challenge.
[4]One chicken died from a coccidia infection and one chicken died due to a crop that was filled with water and no feed.
IM: intramuscular
SQ: subcutaneous
N/A: Not applicable The results show that:

Vaccine A administered by SQ or IM route were effective in reducing and preventing SK colonization in cecum.

Particularly a prevented fraction of about 0.64 was obtained by the IM route and a prevented fraction greater than 0.4 was obtained by the SQ route. FIG. 4 also illustrates an improved protection efficacy against SK for the vaccine with SQ and IM routes (protection SK efficacy >85%, FIG. 4).

4. Protection Against *Salmonella heidelberg* (SH) Infection

TABLE 7

Frequency (%) of reisolation, prevented fraction and 95% Confidence Limits with vaccine A.

| Tissue | Comparison | Proportion Positive | Lower 95% CL[1] | Prevented Fraction | Upper 95% CL[1] |
|---|---|---|---|---|---|
| liver/ | IM | 7/37[2] (19%) | 0.5588 | 0.7694 | 0.9285 |
| spleen | placebo | 32/39 (82%) | N/A[3] | N/A | N/A |
|  | SQ | 5/39 (13%) | 0.6647 | 0.8438 | 0.9658 |
| cecum | placebo | 27/39 (69%) | N/A | N/A | N/A |
|  | SQ | 16/39 (41%) | 0.0684 | 0.4074 | 0.6573 |
| ovaries | IM | 5/37[2] (14%) | 0.4747 | 0.7709 | 0.9293 |
|  | placebo | 23/39 (59%) | N/A | N/A | N/A |
|  | SQ | 3/39 (8%) | 0.6356 | 0.8696 | 0.9816 |

[1]CL = confidence limit
IM: intramuscular
SQ: subcutaneous
N/A: Not applicable

Figure 5A:
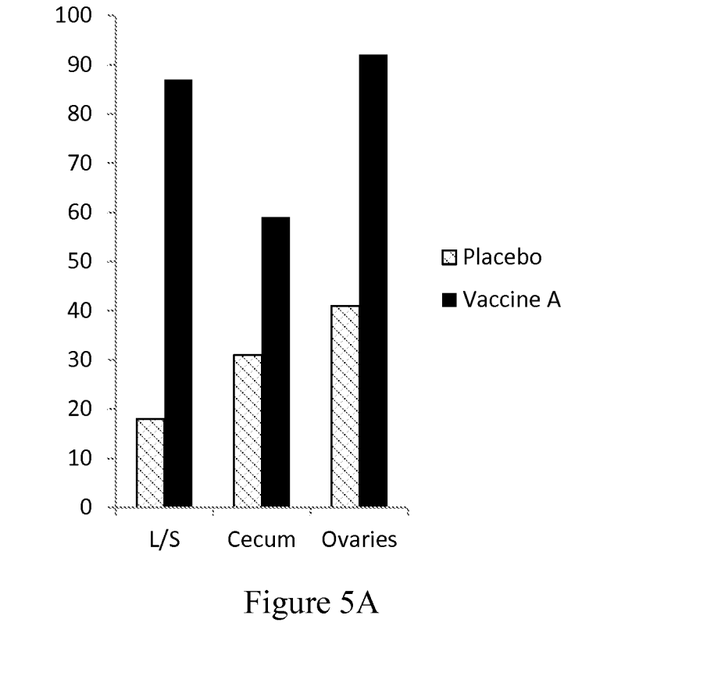
FIGS. 5A-5B: % protection against *Salmonella heidelberg* (SH) in chickens treated with vaccine A by subcutaneous (SQ, FIG. 5A) and intramuscular route (IM, FIG. 5B).
Figure 5B:
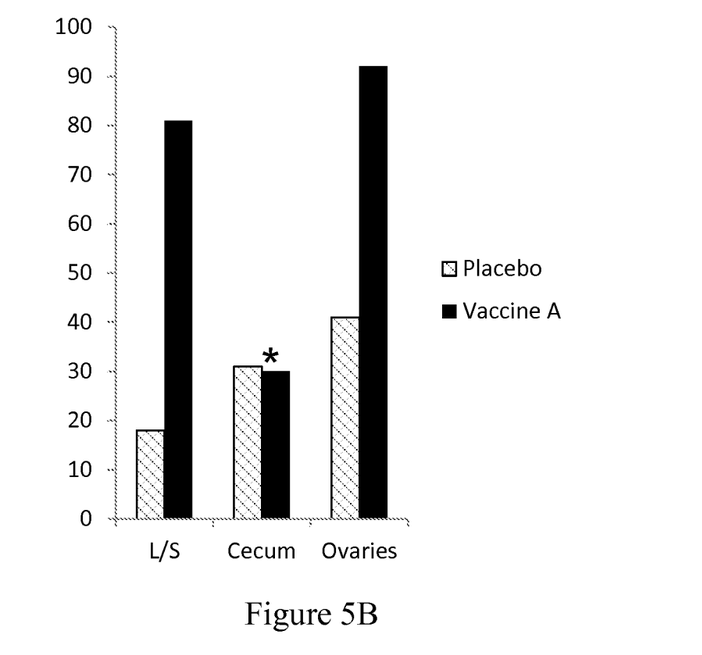

The results show that:

The percent reisolation of the SH challenge strain from the internal organs liver and spleen was 13%, from the cecum was 41% and from the ovaries was 8% in the group vaccinated with vaccine A by the SQ route, and 82%, 69% and 59%, respectively, in the placebo group (FIG. 5A). The lower 95% confidence limit for the preventive fractions was greater than zero for all three tissues. Therefore, vaccine A reduced SH infection in the internal organs, cecum and ovaries when administered by the SQ route. The percent reisolation of the SH strain from the internal organs liver and spleen was 19%, from the cecum was 70% and from the ovaries was 14% in the group vaccinated with vaccine A by the IM route (FIG. 5B). The lower 95% confidence limit for the preventive fractions was greater than zero for the internal organs and the ovaries. Therefore, vaccine A reduced SH infection in the internal organs and ovaries when administered by the IM route.

Vaccine A comprising SE-ST-SK bacterium administered by the IM or SQ route was surprisingly effective in reducing and preventing SH infection of the internal organs (liver/spleen) and ovaries of vaccinated animals.

E. Safety of the Vaccine Compositions

The safety of vaccine A has been analyzed by calculating the intramuscular injection site reactions in pullets. The scoring method is defined in the table 8.

TABLE 8

| External inspection | | Lesions found at dissection | | Extension of lesions (width × length × depth (cm³)) | |
|---|---|---|---|---|---|
| | Score | | Score | | Score |
| Redness | 1 | Diffuse, pinpoint like granulomas (≤1 mm) | 1 | ≤20 | 1 |
| Redness and swelling (soft) | 2 | Diffuse, small granulomas (1-2 mm) | 2 | ≤40 | 2 |
| Redness and swelling (hard) | 3 | Isolated granulomas larger than 2 mm | 3 | ≤60 | 3 |
| Ulcerous | 4 | Inflammatic induration of muscles and colour changes (pale yellow) | 4 | >60 | 4 |

Figure 6:
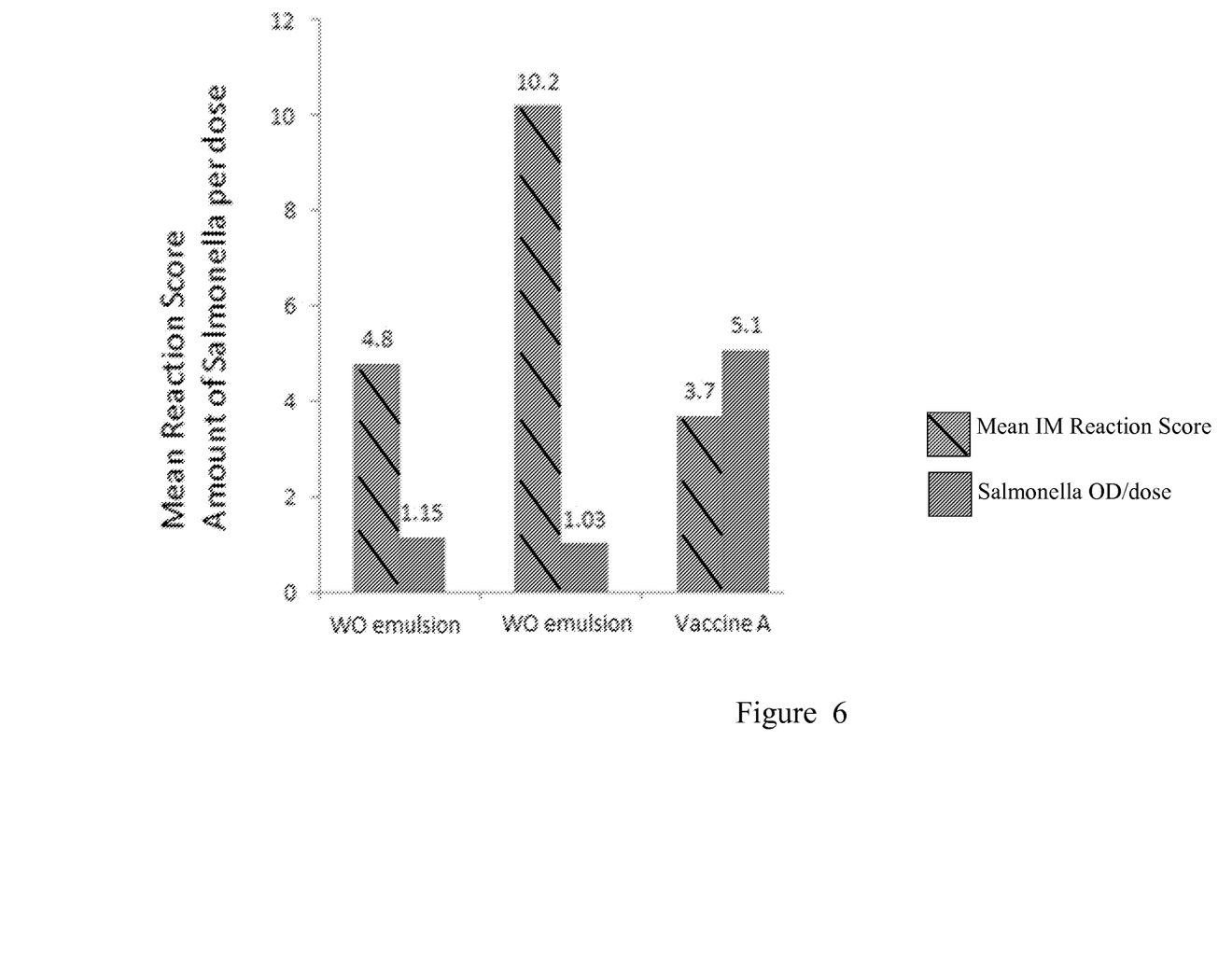
FIG. 6: Intramuscular injection site reactions for vaccine A in pullets.

The results are illustrated in FIG. 6 and show the mean reaction score of vaccines A (SE-ST-SH) compared to prior art vaccines in a simple WO emulsion depending on *Salmonella* OD/dose.

At 1.15 and 1.03 SE OD/dose, vaccines in a simple WO emulsion have a mean reaction score of 4.8 and 10.2, respectively.

The mean reaction score obtained for vaccines A is of 3.7, whereas the *Salmonella* OD/dose is about 5 times more concentrated (5.1).

These results surprisingly showed a weak mean reaction score with intramuscular injections of vaccines of the invention, thereby demonstrating an improved safety.

The invention claimed is:

1. A vaccine comprising an effective amount of at least one antigen and an adjuvant compound in a water-in-oil-in-water (WOW) emulsion, wherein the adjuvant compound is aluminum hydroxide, the at least one antigen is an inactivated *salmonella* bacterium, the WOW emulsion contains oily particles, at least 80% of the oily particles have a size between 3 and 20 µm and at least 60% (w/w) of the total amount of said at least one antigen in the vaccine is contained in the oily particles.

2. The vaccine according to claim 1, wherein said WOW emulsion further comprises at least one surfactant.

3. The vaccine according to claim 1, wherein the oily particles comprise a vegetable oil, an animal oil, a mineral oil, or a mixture thereof.

4. The vaccine according to claim 2, wherein the at least one surfactant is polyoxyethylene sorbitan monooleate or sorbitan monooleate.

5. The vaccine according to claim 1, wherein the WOW emulsion contains water vesicles embedded within the oily particles, said oily particles being dispersed in an outer aqueous phase.

6. The vaccine according to claim 5, wherein between 60% and 75% (w/w) of the total amount of said at least one antigen in the vaccine is contained in the oily particles.

7. The vaccine according to claim 5, wherein the adjuvant compound is in the outer aqueous phase.

8. The vaccine according to claim 1, wherein said vaccine is obtainable by a process comprising:
   a) emulsifying a solution of said at least one antigen in an oil base, thereby forming a water-in-oil (WO) emulsion,
   b) adding said WO emulsion to a dispersal phase, thereby forming a WOW emulsion and emulsifying said WOW emulsion, the WOW emulsion comprising oily particles, and c) mixing said WOW emulsion with the adjuvant compound, wherein at least 60% (w/w) of the total amount of said at least one antigen in the vaccine is contained in the oily particles.

9. A process for the preparation of a vaccine of claim 1, the process comprising the steps of:
   a) emulsifying a solution of said at least one antigen in an oil base, thereby forming a WO emulsion,
   b) adding said WO emulsion to a dispersal phase, thereby forming a WOW emulsion and emulsifying said WOW emulsion, and
   c) mixing said WOW emulsion with an adjuvant compound.

10. A method for vaccinating a non-human animal comprising administering to the animal an effective amount of a vaccine of claim 1.

11. The vaccine according to claim 1, wherein the *salmonella* bacterium is *Salmonella enteritidis, Salmonella kentucky, Salmonella typhimurium, Salmonella heidelberg*, or a combination thereof.

12. The vaccine according to claim 3, wherein the oily particles comprise a mineral oil.

13. The vaccine according to claim 1,
    wherein
       at least 90% of the oily particles in the WOW emulsion have a size between 3 and 20 μm;
       the vaccine has an OD600/ml superior to 4; and
       at least 60% (w/w) of the total amount of said at least one antigen is contained in the oily particles and the rest of said at least one antigen is in the outer aqueous phase with said adjuvant compound.

* * * * *